United States Patent
Steynberg et al.

(12) 
(10) Patent No.: US 6,717,018 B2
(45) Date of Patent: Apr. 6, 2004

(54) PRODUCTION OF OXYGENATED PRODUCTS

(75) Inventors: Jan Petrus Steynberg, Vanderbijlpark (ZA); Khedaren Govender, Vanderbijlpark (ZA); Petrus Johannes Steynberg, Alberton (ZA)

(73) Assignee: Sasol Technology (Proprietary) Limited, Johannesburg (ZA)

( * ) Notice: Subject to any disclaimer, the term of this patent is extended or adjusted under 35 U.S.C. 154(b) by 0 days.

(21) Appl. No.: 10/358,998

(22) Filed: Feb. 5, 2003

(65) Prior Publication Data

US 2003/0158446 A1 Aug. 21, 2003

Related U.S. Application Data

(63) Continuation of application No. PCT/IB01/01452, filed on Aug. 14, 2001.

(51) Int. Cl.[7] .......................... C07C 45/50; C07C 27/20; C07F 15/00; B01J 31/00; B01J 27/185
(52) U.S. Cl. .......................... 568/454; 568/909; 556/16; 502/161; 502/162; 502/213
(58) Field of Search ................. 568/454, 909; 556/16; 502/161, 162, 213

(56) References Cited

U.S. PATENT DOCUMENTS 3,527,818 A    9/1970   Mason et al. ............... 260/632
4,163,760 A *  8/1979   Elsner et al. ............ 260/606.5
5,304,686 A *  4/1994   Slaugh et al. ............... 568/496
6,639,091 B2 * 10/2003  Drent et al. ................. 556/21

FOREIGN PATENT DOCUMENTS

| GB | 1109787 | 4/1968 |
|---|---|---|
| GB | 1254063 | 11/1971 |
| WO | 9845040 | 10/1998 |
| WO | 0116260 | 3/2001 |

* cited by examiner

*Primary Examiner*—Porfirio Nazario-Gonzalez
*Assistant Examiner*—Sikarl A. Witherspoon
(74) *Attorney, Agent, or Firm*—Ladas & Parry

(57) ABSTRACT

A process for producing oxygenated products from an olefinic feedstock, which process includes reacting, in a hydroformylation reaction stage, an olefin feedstock with carbon monoxide and hydrogen at elevated temperature and superatmospheric pressure in the presence of a hydroformylation catalyst. The hydroformylation catalyst comprises a mixture of a metal, M, where M is cobalt (Co), rhodium (Rh), ruthenium (Ru) or palladium (Pd); carbon monoxide; and a bicyclic tertiary phosphine having a ligating phosphorus atom. The ligating phosphorus atom is neither in a bridgehead position nor a member of a bridge linkage. The process produces oxygenated products comprising aldehydes and/or alcohols.

14 Claims, 1 Drawing Sheet

PRODUCTION OF OXYGENATED PRODUCTS

Figure 1:
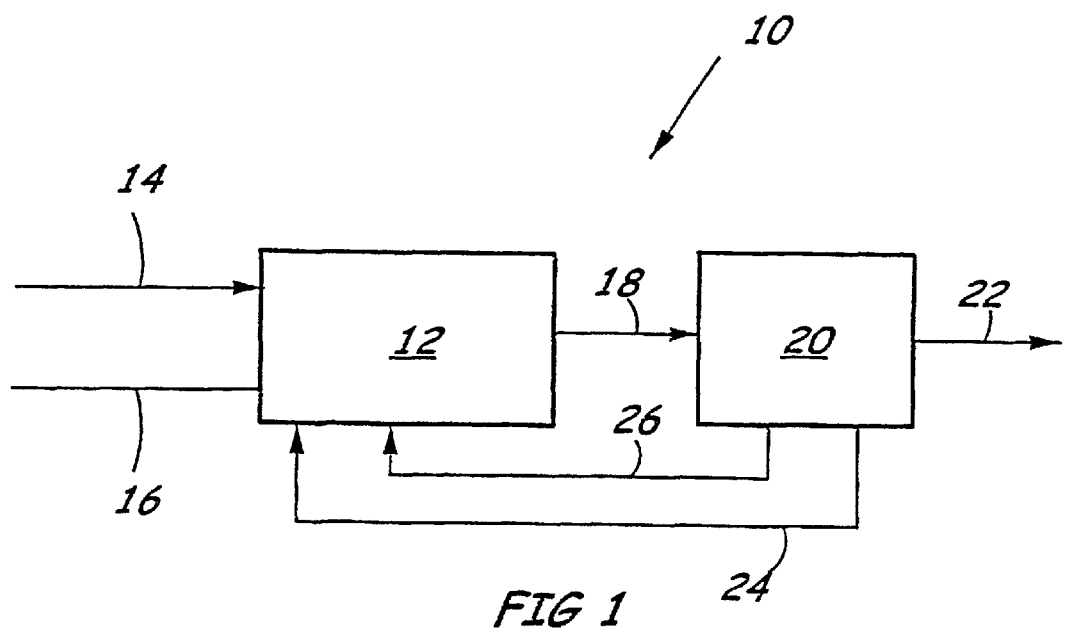

This is a continuation of Application PCT/IB01/01452 filed Aug. 14, 2001.

THIS INVENTION relates to the production of oxygenated products. It relates in particular to a process for producing oxygenated products from an olefinic feedstock, and to a hydroformylation catalyst.

Hydroformylation processes for the production of oxygenated products, particularly aldehydes and/or alcohols, by the reaction of an olefinic feedstock with carbon monoxide and hydrogen at elevated temperatures and pressures in the presence of hydroformylation catalysts, are well known. The alcohols and/or aldehydes that are produced in these processes generally correspond to the compounds obtained, in the hydroformylation reaction, by the addition of a carbonyl or carbinol group to an olefinically unsaturated carbon atom in the feedstock with simultaneous saturation of the olefin bond.

A hydroformylation catalyst is selected according to the particular oxygenated products which are required from a particular olefinic feedstock. Thus, the hydroformylation catalyst may typically be a phosphine and/or phosphite ligand modified rhodium (Rh) or cobalt (Co) homogeneous catalyst. Examples of such catalysts are triphenyl phosphine ligands used with rhodium, and alkyl phosphine ligands used with cobalt. Specific examples of the latter are trialkyl phosphines and bicyclic tertiary phosphines such as 9-phosphabicyclo [3.3.1] nonane and 9-phosphabicyclo [4.2.1] nonane represented by formulas (I) and (II) respectively:

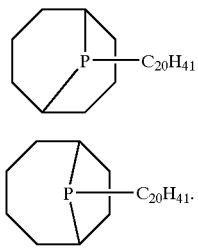

The ligands I and II are available commercially, as a mixture, under the collective chemical name eicosyl phoban ('EP').

A disadvantage of Co catalysed hydroformylation processes is the number of unwanted side reactions that result in the formation of undesirable side products, such as heavy ends and paraffins. These products not only impact negatively on the design of commercial processes but furthermore decrease the yield of the desirable and commercially valuable alcohol and/or aldehyde products from such a process.

Although phosphine-modified Co catalysed hydroformylation affords improved selectivity towards linear alcohols, another disadvantage is that reaction rates are generally far lower than those obtained with unmodified Co catalysis.

It is hence an object of this invention to provide a process for producing oxygenated products from an olefinic feedstock, whereby these problems are at least reduced.

Thus, according to a first aspect of the invention, there is provided a process for producing oxygenated products from an olefinic feedstock, which process includes reacting, in a hydroformylation reaction stage, an olefin feedstock with carbon monoxide and hydrogen at elevated temperature and superatmospheric pressure in the presence of a hydroformylation catalyst comprising a mixture or combination of a metal, M, where M is cobalt (Co), rhodium (Rh), ruthenium (Ru) or palladium (Pd); carbon monoxide; and a bicyclic tertiary phosphine having a ligating phosphorus atom, with the ligating phosphorus atom being neither in a bridgehead position nor a member of a bridge linkage, to produce oxygenated products comprising aldehydes and/or alcohols.

The metal, M, may be any one of cobalt, rhodium, ruthenium or palladium; however, cobalt is preferred.

In particular, the bicyclic tertiary phosphine of the hydroformylation catalyst may be a [3.3.1]phosphabicyclononane represented by formula (III):

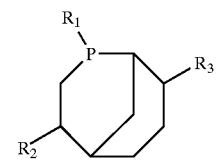

where
$R_1$ is an alkyl, branched alkyl, cycloalkyl, or aryl group;
$R_2$ is an alkyl group; and
$R_3$ is an alkyl group.

More particularly, $R_1$ of the [3.3.1]phosphabicyclononane of formula (III) may be a linear $C_2$ to $C_{20}$ hydrocarbon chain; and $R_2=R_3$. Still more particularly, $R_2$ and $R_3$ may each be methyl.

The family of ligands of formula (Ill) in which $R_2=R_3=$ methyl is named Lim (as these ligands are limonene derived); thus, each ligand can be denoted 'Lim', together with a suffix corresponding to the carbon number of $R_1$. In one embodiment of the invention, the ligand may be Lim-18. Thus, Lim-18 will be represented by the formula IV, where $R_1$ is $C_{18}H_{37}$.

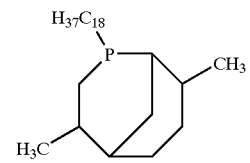

In another embodiment of the invention, the ligand may be Lim-10. In other words, $R_1$ of the [3.3.] phosphabicyclononane of formula (III) is then $C_{10}H_{21}$.

The reaction temperature may be from 100° C. to 300° C., typically from 150° C. to 200° C.

The reaction pressure may be at least 20 bar (150 psi), preferably between 50 bar (750 psi) and 100 bar (1500 psi), typically about 85 bar (1232 psi).

The hydroformylation reaction stage may be provided by a reactor capable of handling a homogenously catalysed chemical transformation, such as a continuous stirred tank reactor ('CSTR'), bubble column, or the like.

The olefinic feedstock may, in particular, be a $C_2$ to $C_{20}$ Fischer-Tropsch derived olefin stream. Thus, the olefinic feedstock may be that obtained by subjecting a synthesis gas comprising carbon monoxide and hydrogen to Fischer-Tropsch reaction conditions in the presence of an iron-based, a cobalt-based or an iron/cobalt-based Fischer-Tropsch catalyst, with the resultant olefinic product then constituting the olefinic feedstock of the process of the invention, or a component thereof constituting the olefinic feedstock of the process of the invention.

In other words, the olefinic product from the Fischer-Tropsch reaction can, if necessary, be worked up to remove unwanted components therefrom and/or to separate a particular olefinic component therefrom, with said particular olefinic component then constituting the olefinic feedstock of the process of the invention.

According to a second aspect of the invention, there is provided a hydroformylation catalyst which includes, as a first component, a metal M, where M is cobalt, rhodium, ruthenium, or palladium; as a second component, carbon monoxide; and, as a third component, a bicyclic tertiary phosphine having a ligating phosphorus atom, with the ligating phosphorus atom being neither in a bridgehead position nor a member of a bridge linkage, to produce oxygenated products comprising aldehydes and/or alcohols, with the components being in the form of a mixture.

The metal M and the bicyclic tertiary phosphine may be as hereinbefore described with respect to the first aspect of the invention.

The invention will now be described by way of example, with reference to the following drawings.

Figure 2:
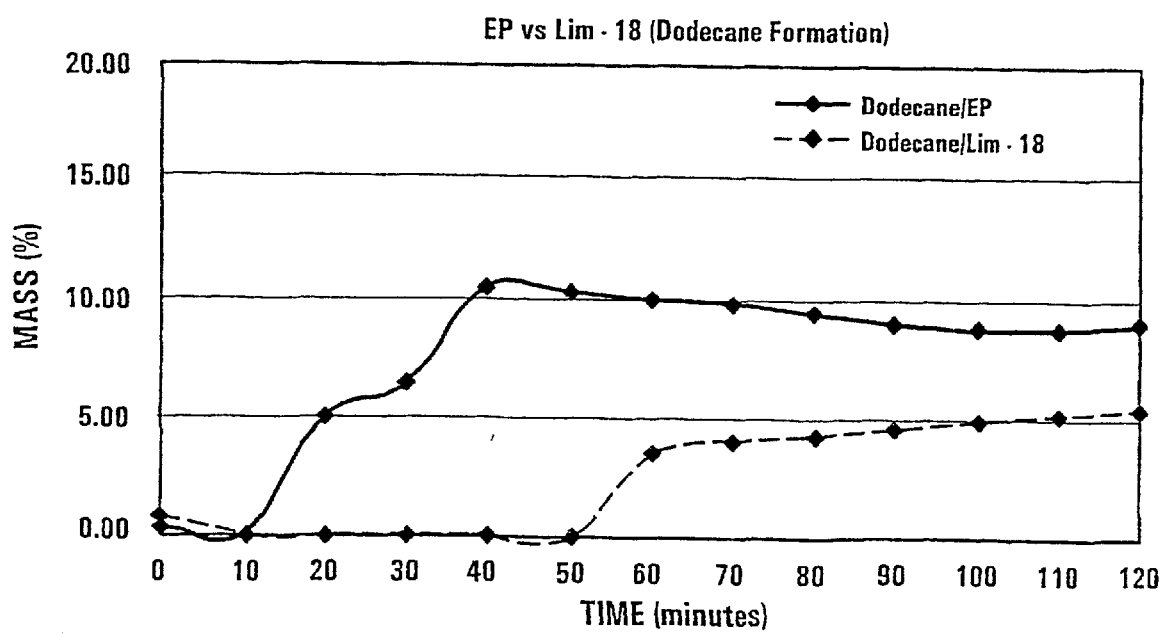

In the drawings,

FIG. 1 shows a simplified flow diagram of a process according to the invention for producing, oxygenated products from an olefinic feedstock; and FIG. 2 shows, for Example 6, the formation of side products with time for Lim-18.

Referring to FIG. 1, reference numeral 10 generally indicates a process according to the invention for producing oxygenated products from an olefinic feedstock.

The process 10 includes a hydroformylation stage 12, with an olefinic feedstock flow line 14 as well as a synthesis gas feed line 16 leading into the stage 12. A product withdrawal line 18 leads from the hydroformylation stage 12.

The process 10 includes a separation stage 20 into which the line 18 leads, with a product withdrawal line 22 leading from the stage 20. An unreacted feedstock recycle line 24, for recycling unreacted feedstock which is separated from the product produced, leads from the stage 20 back to the stage 12. A catalyst recycle line 26 also leads from the stage 20 back to the stage 12, for recycling, catalyst which is separated from the product in the stage 20, back to the stage 12.

In use, a Fischer-Tropsch derived olefinic feedstock is fed into the stage 12 along the flow line 14, as is a synthesis gas comprising a mixture of carbon monoxide and hydrogen, which enters the stage 12 along the flow line 16. In the stage 12, the olefinic feedstock reacts with the carbon monoxide and hydrogen in the presence of a catalyst comprising an intimate mixture or combination of cobalt, carbon monoxide and a bicyclic tertiary phosphine having formula (IV), ie Lim-18, hereinbefore described. The temperature in the hydroformylation stage 12 is typically around 170° C., while the pressure is typically around 85 bar (1232 psi). Oxygenated products, consisting mainly of alcohols, are produced, and are withdrawn along the line 18 for further work-up.

The hydroformylation reaction stage 12 typically comprises a hydroformylation reactor system incorporating catalyst recovery and/or catalyst recycle.

EXAMPLES

In the Examples hereinafter given, all reactions were carried out in a 300 ml stainless steel stirred autoclave operated at 1200 rpm at the desired constant pressure with syngas delivered on demand. For each run the olefin, paraffinic solvent, and required amount of catalyst stock solution were loaded into the autoclave under argon, the reactor closed and purged with syngas, ie synthesis gas comprising a mixture of carbon monoxide and hydrogen, and then heated to the desired reaction temperature at atmospheric or ambient pressure. The reactions were initiated by pressurising with syngas to the desired reaction pressure. The syngas employed was a commercially available 2:1 mixture of hydrogen and carbon monoxide. Catalyst stock solutions were prepared using cobalt (2) octanoate and the appropriate ligand (EP, Lim-18 or Lim-10) in the required ratios. The olefins employed were 1-dodecene and a Fischer-Tropsch derived $C_{13/14}$ olefin feedstock.

Example 1
Comparative Example

Hydroformylation of 1-dodecene was carried out out in the manner described above. Using standard conditions of 85 bar of 2:1 $H_2$:CO syngas, 1000 ppm Co and a 2:1 ligand to metal molar ratio, hydroformylations were carried out at different temperatures to determine reaction rate and conversions. Rate constants were determined from analysis of gas uptake data, and conversions were based on GC analysis of samples taken at 2 hours. Results are summarised in Table 1.

TABLE 1

Comparative catalyst reactivity in hydroformylation of 1-dodecene

| Ligand/Temperature (° C.) | k' (h$^{-1}$) | Conversion |
| --- | --- | --- |
| Lim-18/170° C. | 0.82 | 99% |
| EP/170° C. | 0.46 | 74% |
| Lim-18/180° C. | 1.54 | 99% |
| EP/180° C. | 0.70 | 87% |
| Lim-18/190° C. | 2.69 | 100% |
| EP/190° C. | 1.14 | 96% |

Example 2
Comparative Example

Hydroformylation of 1-dodecene was carried out out in the manner described above. Using standard conditions of 170° C., 85 bar of 2:1 $H_2$:CO syngas and 1000 ppm Co, the ligand to metal ratio was changed. Paraffin formation was determined from GC analysis of the hydroformylation reaction mixture sampled after 2 hours. Results are summarised in Table 2.

TABLE 2

Paraffin formation in hydroformylation of 1-dodecene

| Ligand/L:M | Paraffin (mass %) |
|---|---|
| Lim-18/2:1 | 5.39 |
| EP/2:1 | 8.50 |
| Lim-18/4:1 | 6.98 |
| EP/4:1 | 10.99 |
| Lim-18/8:1 | 8.12 |
| EP/8:1 | 11.43 |

As seen from Table 2, an undesirable side-reaction where a portion of the olefinic feedstock (1-dodecene) is converted to a saturated hydrocarbon (dodecane) is much less prominent when the LIM-18 catalyst system is employed in the hydroformylation process.

Example 3
Comparative Example

Exhaustive hydroformylation of 1-dodecene was carried out in the manner described above, with reaction conditions of 170° C., 85 bar of 2:1 $H_2$:CO syngas, 1000 ppm Co and 2:1 ligand to metal molar ratio. High temperature GC analysis of the reaction mixtures was carried out to quantify formation of heavy ends. As seen from Table 3, the formation of unwanted "heavies" fractions are suppressed when the LIM catalyst system is employed.

TABLE 3

Heavies formation in hydroformylation of 1-dodecene

| LIGAND | HEAVIES (mass %) |
|---|---|
| EP | 1.56% |
| Lim-18 | 1.36% |

Example 4

Hydroformylation of a Fischer-Tropsch-derived $C_{13/14}$ olefin feed was carried out in the manner described above using Lim-18 as ligand, with reaction conditions of 170° C., 85 bar of 2:1 $H_2$:CO syngas, 1000 ppm Co and 2:1 ligand to metal molar ratio. As can be seen from Table 4, the calculated k' values for this reaction compare very well to those obtained from pure feedstock.

TABLE 4

Comparison of feedstocks

| Feedstock | k' ($h^{-1}$) |
|---|---|
| $C_{13/14}$ Fischer-Tropsch-derived | 0.81 |
| 1-dodecene | 0.82 |

Example 5

Hydroformylation of 1-dodecene was carried out in the manner described above using Lim-10 as ligand, with reaction conditions of 170° C., 85 bar of 2:1 $H_2$:CO syngas, 1000 ppm Co and 2:1 ligand to metal molar ratio. As can be seen in Table 5, a ligand with a shorter alkyl chain affords comparable reactivity.

TABLE 5

Effect of ligand alkyl chain

| Ligand | k' ($h^{-1}$) |
|---|---|
| Lim-18 | 0.82 |
| Lim-10 | 0.80 |

Example 6

A sampling run in a 600 ml autoclave was carried out for hydroformylation of 1-dodecene using Lim-18 as ligand. Reaction conditions of 170° C., 85 bar of 2:1 $H_2$:CO syngas, 1000 ppm Co and 2:1 ligand to metal molar ratio were employed, and samples were taken at various time intervals and analysed by GC to determine paraffin make with time. The results are indicated in FIG. 2.

Example 7

Hydroformylation of 1-dodecene was carried out in the manner described above, with reaction conditions of 170° C., 85 bar of 2:1 $H_2$:CO syngas, 1000 ppm Co and 4:1 ligand to metal molar ratio. As can be seen in Table 6, ligands in accordance with the invention and where $R_1$ is not a linear alkyl chain (in this example, aryl or cycloalkyl) provide comparable reactivities.

TABLE 6

Effect of $R_1$

| Ligand/$R_1$ | k' ($h^{-1}$) |
|---|---|
| III/phenyl | 0.41 |
| III/cyclopentyl | 0.44 |
| Lim-18 | 0.36 |

Thus, it has surprisingly been found that reaction rate is increased and the number of side reactions in the hydroformylation process is reduced is if a novel catalyst consisting of a complex mixture of cobalt, carbon monoxide and a bicyclic tertiary phosphine where the ligating phosphorus atom is neither in a bridgehead position nor a member of a bridge linkage, is used as a hydroformylation catalyst, with either pure olefinic feedstocks or with olefinic feedstocks derived from Fischer-Tropsch processes. While the phosphorus atoms in ligands (I) and (II) are bridge linkages and thus shared between both heterocyclic rings, the ligating phosphorus atom in ligands (III) and (IV) forms part of only one ring in the bicyclic system. In contrast to ligands (I) and (II) where the phosphorus atom is flanked by two tertiary carbons, the ligating phosphorus atom is connected to a tertiary as well as to a secondary carbon atom in ligands (III)/(IV). It was thus surprisingly found that these structural differences resulted in an improved catalyst system so that these structural differences are thus apparently critical.

What is claimed is:

1. A process for producing oxygenated products from an olefinic feedstock, which process includes reacting, in a hydroformylation reaction stage, an olefin feedstock with carbon monoxide and hydrogen at elevated temperature and superatmospheric pressure in the presence of a hydroformylation catalyst comprising a mixture or combination of a metal, M, where M is cobalt (Co), rhodium (Rh), ruthenium (Ru) or palladium (Pd); carbon monoxide; and a bicyclic tertiary phosphine having a ligating phosphorus atom and being a [3.3.1]phosphabicyclononane represented by formula (III):

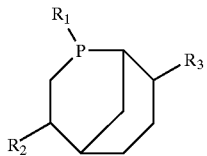

III where
- $R_1$ is an alkyl, branched alkyl, cycloalkyl, or aryl group;
- $R_2$ is an alkyl group; and
- $R_3$ is an alkyl group, to produce oxygenated products comprising aldehydes and/or alcohols.

2. A process according to claim 1, wherein, in the hydroformylation catalyst, M is cobalt.

3. A process according to claim 1, wherein, in the hydroformylation catalyst, $R_1$, $R_2$ and $R_3$ of the [3.3.1]phosphabicyclononane of formula (III) are, respectively, an alkyl group, methyl and methyl.

4. A process according to claim 1, wherein, in the hydroformylation catalyst, $R_1$ of the [3.3.1]phosphabicyclononane of formula (III) is a linear $C_2$ to $C_{20}$ hydrocarbon chain.

5. A process according to claim 4, wherein, in the hydroformylation catalyst, $R_1$ of the [3.3.1]phosphabicyclononane of formula (III) is $C_{18}H_{37}$.

6. A process according to claim 4, wherein, in the hydroformylation catalyst, $R_1$ of the [3.3.1]phosphabicyclononane of formula (III) is $C_{10}H_{21}$.

7. A process according to claim 1, wherein the reaction temperature is from 100° C. to 300° C., while the reaction pressure is at least 20 bar.

8. A process according to claim 1, wherein the olefinic feedstock is a $C_2$ to $C_{20}$ Fischer-Tropsch derived olefinic stream.

9. A hydroformylation catalyst which includes, as a first component, a metal M, where M is cobalt, rhodium, ruthenium, or palladium; as a second component, carbon monoxide; and, as a third component, a bicyclic tertiary phosphine having a ligating phosphorus atom and being a [3.3.1]phosphabicyclononane represented by formula (III):

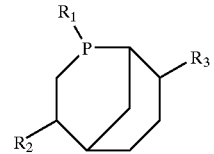

III where
- $R_1$ is an alkyl, branched alkyl, cycloalkyl, or aryl group;
- $R_2$ is an alkyl group; and
- $R_3$ is an alkyl group, with the components being in the form of a mixture.

10. A hydroformylation catalyst according to claim 9, wherein M is cobalt.

11. A hydroformylation catalyst according to claim 9, wherein $R_1$, $R_2$ and $R_3$ of the [3.3.1]phosphabicyclononane of formula (III) are, respectively, an alkyl group, methyl and methyl.

12. A hydroformylation catalyst according to claim 9, wherein $R_1$ of the [3.3.1]phosphabicyclononane of formula (III) is a linear $C_2$ to $C_{20}$ hydrocarbon chain.

13. A hydroformylation catalyst according to claim 12, wherein $R_1$ of the [3.3.1]phosphabicyclononane of formula (III) is $C_{18}H_{37}$.

14. A hydroformylation catalyst according to claim 12, wherein $R_1$ of the [3.3.1]phosphabicyclononane of formula (III) is $C_{10}H_{21}$.

* * * * *

UNITED STATES PATENT AND TRADEMARK OFFICE
CERTIFICATE OF CORRECTION

PATENT NO. : 6,717,018 B2 Page 1 of 1
DATED : April 6, 2004
INVENTOR(S) : Jan Petrus Steynberg et al.

It is certified that error appears in the above-identified patent and that said Letters Patent is hereby corrected as shown below:

<u>Title page,</u>
Insert Item -- [30] Foreign Application Priority Data, Aug. 14, 2001 (ZA) ....2000/4131 --.

Signed and Sealed this

Twenty-fifth Day of April, 2006

JON W. DUDAS
*Director of the United States Patent and Trademark Office*